United States Patent [19]

Klinkmann et al.

[11] 4,453,020

[45] Jun. 5, 1984

[54] PROCESS FOR PURIFYING THE METHANOL EMPLOYED IN THE PREPARATION OF FORMALDEHYDE

[75] Inventors: Kurt Klinkmann, Cologne, Fed. Rep. of Germany; Paul R. Wambach, deceased, late of Leverkusen, Fed. Rep. of Germany, by Christa Wambach, legal representative

[73] Assignee: Bayer Aktiengesellschaft, Leverkusen, Fed. Rep. of Germany

[21] Appl. No.: 411,397

[22] Filed: Aug. 25, 1982

Related U.S. Application Data

[63] Continuation-in-part of Ser. No. 354,841, Mar. 4, 1982, abandoned.

[30] Foreign Application Priority Data

Mar. 19, 1981 [DE] Fed. Rep. of Germany ....... 3110723

[51] Int. Cl.$^3$ ............................................ C07C 47/052
[52] U.S. Cl. ..................................... 568/473; 568/472; 568/474; 568/917
[58] Field of Search ................ 568/917, 472, 473, 474

[56] References Cited

U.S. PATENT DOCUMENTS

| | | | |
|---|---|---|---|
| 1,738,745 | 12/1929 | Weith et al. | 568/472 |
| 2,628,986 | 2/1953 | Wallace et al. | 568/917 |
| 2,792,344 | 5/1957 | Tidwell | 568/917 |
| 3,373,180 | 3/1968 | Glass et al. | 568/917 |
| 3,433,841 | 3/1969 | Dehn et al. | 568/917 |
| 4,208,353 | 6/1980 | Webster et al. | 568/472 |

FOREIGN PATENT DOCUMENTS

| | | | |
|---|---|---|---|
| 689920 | 6/1964 | Canada | 568/473 |
| 1101383 | 3/1961 | Fed. Rep. of Germany | 568/917 |
| 1235881 | 3/1967 | Fed. Rep. of Germany | 568/473 |
| 1277834 | 9/1968 | Fed. Rep. of Germany | 568/473 |
| 38-15355 | 8/1963 | Japan | 568/917 |
| 253040 | 2/1970 | U.S.S.R. | 568/917 |
| 288741 | 1/1972 | U.S.S.R. | 568/917 |

*Primary Examiner*—J. E. Evans
*Attorney, Agent, or Firm*—Sprung, Horn, Kramer & Woods

[57] ABSTRACT

The invention relates to a process for purifying, by treatment with an acid ion exchanger and, if desired, a basic ion exchanger, the methanol employed in the preparation of formaldehyde.

13 Claims, No Drawings

PROCESS FOR PURIFYING THE METHANOL EMPLOYED IN THE PREPARATION OF FORMALDEHYDE

CROSS REFERENCE TO RELATED APPLICATION

This is a continuation-in-part of copending application Ser. No. 354,841, filed Mar. 4, 1982 entitled "Process for purifying methanol employed in the preparation of formaldehyde", now abandoned.

BACKGROUND OF THE INVENTION

1. Field of the Invention

The invention relates to a process for purifying the methanol employed in the preparation of formaldehyde.

2. Discussion of Prior Art

It is known that the starting materials required for the preparation of formaldehyde must be very pure, in order not to impair the activity and life of the silver catalyst to an excessive extent (compare, for example, (Auslegeschrift 2,323,758). The methanol or methanol/water mixture employed for the reaction, in addition to a number of organic substances, virtually always contains a number of inorganic compounds which, for example, promote side reactions which reduce the yield, or act as catalyst poisons. It is, therefore, necessary to purify the methanol before the oxidation and to use very pure water for the preparation of the methanol/water mixture or to subject the methanol/water mixture to subsequent purification.

Thus Auslegeschrift 1,235,881 discloses a process for the preparation of formaldehyde, in which the crude methanol is treated with alkali before, during and/or after removing a fraction boiling lower than methanol, and before the reaction to give formaldehyde. A similar method of purification is also disclosed in British 344,796. In accordance with this Patent, crude methanol, for example, containing traces of iron as an impurity, is likewise treated with alkalis. However, the purification with alkalis has the disadvantage that large quantities of strongly alkaline effluents are produced, the removal of which requires considerable technical outlay, to the detriment of the cost-efficiency of such purification processes.

Another possible means of purifying crude methanol consists in treatment with oxidizing agents. For example, purification of the crude methanol by treatment with chromic acid is disclosed in British No. 500,745, purification with permanganate and zinc chloride is disclosed in German No. 625,324 and purification by treatment with gas containing ozone is disclosed in Auslegeschrift No. 1,152,392. It is stated in German Auslegeschrift No. 1,231,677 to be particularly effective to purify crude methanol by treatment with oxygen or hydrogen peroxide in the presence of substances having a large surface area, such as silica gel, kieselguhr, alumina, earthy cerussite or active charcoal.

However, the purification processes mentioned have the disadvantage that effluent problems arise if chromic acid or permanganate are used. In addition, traces of chromic acid and permanganate, remaining in the treated methanol, can impair the activity of the sensitive silver catalyst. Nor does the use of ozone or hydrogen peroxide in treating the crude methanol bring any kind of advantage, since, on the one hand, these compounds are relatively expensive chemicals, which cannot be recovered after the treatment, and, on the other hand, only oxidisable substances can be removed thereby.

As can be seen from German Auslegeschrift No. 2,323,758, column 4, lines 14–29, in spite of purifying the crude methanol with the compounds mentioned above, the life of the silver catalyst, and also the yields and space/time yields of pure formaldehyde achieved with the catalyst, are still unsatisfactory, since some of the impurities contained in the crude methanol are not removed and deactivate the catalyst during the reaction.

SUMMARY OF THE INVENTION

A process for purifying the methanol or methanol/water mixture employed in the preparation of formaldehyde has now been found, which is characterized in that the methanol or methanol/water mixture to be oxidized is treated before evaporation, with an acid ion exchanger and, if desired, a basic ion exchanger.

The acid ion exchangers employed in the process according to the invention can, for example, be the commercially available acid, macroporous or gel-type exchangers in the $H^{(+)}$ form, based on crosslinked polystyrene resins containing sulphonic acid groups (strongly acid ion exchangers) or based on crosslinked polyacrylic acids containing carboxyl groups (weakly acid ion exchangers), such as are described, for example, in Ullmanns Encyklopädie der technischen Chemie ("Ullmanns Encyclopaedia of Industrial Chemistry"), 4th edition, Volume 13, pages 279–346, the disclosure of which is thereby encorporated herein by preference.

Strongly acid, macroporous cation exchangers are preferably employed in the process according to the invention.

The basic ion exchangers employed can be, for example, the commercially available basic, macroporous or gel-type anion exchangers based on crosslinked polystyrene or polyacrylamide resins containing quaternary ammonium groups (strongly basic) or based on crosslinked polystyrene or polyacrylamide resins containing amino groups (weakly basic), such as are described, for example, in Ullmanns Encyklopädie der technischen Chemie ("Ullmanns Encyclopaedia of Industrial Chemistry"), 4th edition, Volume 13, pages 279–346.

Strongly basic, macroporous anion exchangers are preferably employed in the process according to the invention.

About 100 to 200 l (l=liter), preferably 150 to 180 l, of acid ion exchangers are employed for treating the methanol or methanol/water mixture in the process according to the invention.

If these quantities of acid ion exchangers are employed the throughput of anhydrous or aqueous methanol can be about 500 to 10,000 l/hour, preferably 2,000 to 5,000 l/hour. It is, of course, also possible to employ smaller or larger quantities of acid ion exchangers, the throughput of anhydrous or aqueous methanol then being correspondingly decreased or increased.

The treatment of the methanol or methanol/water mixture with the acid ion exchangers is generally carried out at temperatures of about 0° to 60° C., preferably at 15° to 40° C., and the process is advantageously carried out under normal pressure.

If the methanol or methanol/water mixture to be reacted is also treated, additionally, with basic ion exchangers, 100 to 200 l, preferably 150 to 180 l, of basic ion exchangers are similarly employed. Here too, if it appears appropriate, either smaller or larger quantities of basic ion exchangers can be employed, the throughput of anhydrous or aqueous methanol being correspondingly reduced or increased, of course. If the quantity of basic ion exchangers indicated above is employed, the throughput of anhydrous or aqueous methanol can be about 300 to 3,000 l/hour, preferably 400 to 800 l/hour.

The treatment with basic ion exchangers is usually carried out at temperatures of about 0° to 70° C., preferably at 20° to 65° C., and under normal pressure.

However, it is also possible to carry out the process under an elevated pressure of about 0.1 to 5, preferably 2 to 3, bars, temperatures of about 90° to 100° C. being most advantageous. The use of pressure is advantageous, since this enables the throughput of methanol or methanol/water mixture to be increased considerably without thereby impairing the purifying action.

If aqueous methanol is employed in the reaction, its concentration is about 50 to 90, preferably 55 to 70, % by weight.

The treatment of the methanol or methanol/water mixture with the acid ion exchangers and, if appropriate, the basic ion exchangers can be effected in the customary ion exchange equipment and in accordance with customary methods of treatment. The methanol or methanol/water mixture can be treated first with the acid ion exchanger and subsequently, if necessary, with the basic ion exchanger. The converse mode of treatment is, of course, also possible. Treatment first with alkaline ion exchangers and then with acid ion exchangers is preferred for practical reasons. Furthermore, it is possible to carry out the treatment of the methanol or methanol/water mixture in a mixed bed or layered bed apparatus.

The treatment, according to the invention, of the methanol or methanol/water mixture can be carried out either continuously or discontinuously.

For example, the treatment of the aqueous methanol (concentration of methanol approx. 56% by weight) can be carried out by pumping the methanol at 40°-100° C., preferably at 50°-60° C., and under a pressure of up to approx. 10 bars, through a container filled with 1,200 l of strongly basic ion exchanger, at a rate of 4,000 l/hour, and then passing the aqueous methanol treated in this way, at room temperature and under a pressure of up to 10 bars, through a container filled with 200 l of strongly acid ion exchanger, at a rate of 4,000 l/hour.

The aqueous methanol obtained thereby can then be vaporized directly without further purification and can be converted into formaldehyde on the silver contact catalyst, such as by oxygen gas (air) vapor phase oxidation.

DESCRIPTION OF PREFERRED EMBODIMENT

In a preferred embodiment, this invention contemplates a process for preparing formaldehyde which comprises:

(A) vaporizing a portion of methanol or a methanol/water mixture feed into a vaporizer whereby some of the methanol or methanol/water mixture remain in liquid phase;

(B) passing the vapor containing methanol or methanol/water mixture to a reaction vessel to which oxygen or an oxygen containing gas is introduced and therein converting the methanol to formaldehyde;

(C) withdrawing at least a portion of said liquid phase and passing said liquid phase over an acid and/or a basic ion exchanger; and (D) recycling the liquid phase after contact with said acid and/or basic ion exchanger to said vaporizer.

The liquid phase can be recycled to the vaporizer by passing it through a bed of acid and/or basic ion exchanger through which fresh methanol or methanol/water mixture is passed. Alternatively or additionally, the liquid phase can be recycled through a separate bed of acid and/or basic ion exchanger and then directly or indirectly fed to a vaporizer. The vaporizer can be the same vaporizer through which fresh methanol or methanol/water mixture is passed. Acid and/or basic ion exchangers useful for treatment of the liquid phase from the vaporizers include those useful in treatment of the fresh methanol or methanol/water treatment.

Generally the vaporizer is operated at a temperature of 60° to 100° C., preferably 65° to 75° C. and at an absolute pressure of 0.5 to 2.0 atmospheres, preferably 0.7 to 1.5 atmospheres. The feed rate, depending on the size of the vaporizer, of methanol or methanol/water mixture is generally 1000 to 4000 liters/hour, preferably 1500 to 4000 liters/hour.

The remaining unvaporized (liquid) phase is passed through an acid and/or basic ion exchanger at a feed rate (depending on the size of the ion exchanger bed) of 500 to 1500 liters/hour, preferably 800 to 1200 liters/hour. The liquid phase is generally at a temperature of 65° to 75° C. When the process is operated using a mixture of methanol and water the mixture generally contains 55 to 70 weight percent, preferably 60 weight percent methanol.

The process can be conducted by continuously or intermittently withdrawing liquid phase from the sump of the vaporizer and continuously or intermittently recycled via the acid and/or basic ion exchanger the vaporizer.

Compared with the processes known hitherto from the state of the art for preparing formaldehyde from methanol, which purify the methanol to be reacted, for example, by distillation or treatment with alkalis or oxidizing agents, the process according to the invention achieves a substantially increased catalyst life (an increase from 120 days in accordance with German Offenlegungsschrift No. 2,137,938 to at least 166 days in accordance with the process according to the invention, in which connection it should be noted that the test had to be discontinued because of a technical breakdown, although the catalyst was still fully active) and a higher yield of formaldehyde. In addition, the treatment of the methanol or methanol/water mixture in accordance with the invention makes it possible to reduce the residual content of methanol in the formaldehyde to less than 1% by weight (determined by gas chromatography). Since only small quantities of methanol still remain in the formaldehyde, it is possible in virtually all cases to subject the formaldehyde directly to further reactions, without the methanol manifesting itself as a problem.

As a result of the increases in the yield of formaldehyde achieved with the aid of the process according to the invention, and as a result of the longer catalyst service lives obtained, the capacity of an existing plant is increased by about 10%, which constitutes an additional economic advantage.

Although the treatment of the methanol in the process according to the invention is carried out with ion exchangers composed of organic polymers and it was thus necessary to assume that traces of the ion exchanger material would dissolve in the methanol and thereby impair the activity of the sensitive silver catalyst, it is extremely suprising for those skilled in the art, that, contrary to expectation, the life of the silver catalyst was increased considerably and the yield of formaldehyde was improved.

The example given below is intended to illustrate the process according to the invention.

EXAMPLE

The aqueous, distilled methanol (% content of methanol approx. 56% by weight) intended for the preparation of formaldehyde is treated continuously, at a temperature of 15° to 30° C., with a strongly acid cation exchanger in the H⊕ form, based on a polystyrene/divinylbenzene resin containing sulphonic acid groups (commercially available, for example, as Lewatit® SC 108, S 100, SP 112 and SP 120; charge: 300 l; throughput: 4,000 l/hour) and is then passed directly into the vaporizer of an industrial formaldehyde plant. In addition, the vaporizer sump product continuously circulated by pumping at a rate of 1,000 l/hour through a container filled with 120 l of strongly acid cation exchanger (H+ form). The resulting acid exchanger treated methanol/water mixture is thereafter recycled directly back to the vaporizer. The methanol/water mixture vaporized in the vaporizer, to which air was also added, is blown over a silver contact catalyst corresponding to the silver catalyst decribed in German No. 1,285,995, Example 1.

The reaction at the catalyst is carried out under a pressure of about 150 to 300 mbars and at a temperature of 660° to 670° C., using a mixture consisting of: 2,060 kg/hour of methanol vapor, 1,586 kg/hour or steam and 4,020 kg/hour of air. The reaction gases-formaldehyde, water and residual methanol-is condensed in a customary adsorption plant after being cooled in the reactor condenser, and the exit gas is additionally washed with water, which was re-used for absorbing formaldehyde.

During an operating time of 166 days, an approx. 37.5% strength by weight formaldehyde solution having a residual methanol content of 0.6 to 0.9% by weight is obtained continuously. The table below shows how the residual methanol content in the formaldehyde solution is altered during this time:

| | Residual methanol content (determined by gas chromatography in % by weight | Formaldehyde concentration in % by weight |
|---|---|---|
| 1st day | 0.6 | 37.3 |
| 10 days | 0.7 | 37.5 |
| 50 days | 0.6 | 37.1 |
| 100 days | 0.7 | 37.8 |
| 120 days | 0.8 | 37.3 |
| 140 days | 0.9 | 37.5 |
| 150 days | 0.9 | 37.3 |
| 160 days | 0.9 | 37.4 |
| 166 days | 0.9 | 37.2 |

During this operating time, the yield of formaldehyde varies between 89 and 91% of theory.

If aqueous methanol intended for conversion, which had been purified by distillation, but still contained traces of iron carbonyl (approx. 1.5 mg of Fe/l), was also treated, additionally, with a strongly basic ion exchanger in order to remove the iron carbonyl compounds from the methanol, the formaldehyde solution obtained also had a residual methanol content of 0.6 to 0.9% by weight. The yield of formaldehyde also varied between 89 and 91% of theory.

The test had to be discontinued after 166 days owing to a technical breakdown. At this point in time the catalyst was still fully active. The catalyst was virtually free from troublesom metallic or carbonaceous deposits.

COMPARISON EXAMPLE

The aqueous, distilled methanol (methanol content approx. 56% by weight) intended for the preparation of formaldehyde, was passed, at room temperature, direct into the vaporizer of an industrial formaldehyde plant, air being blown into the vaporizier at the same time. The silver catalyst corresponded to the catalyst described in German No. 1,285,995, Example 1. The reaction at the catalyst was carried out under a pressure of about 100 to 300 mbars and at a temperature of about 650° to 680° C., using a mixture consisting of: 2,060 kg/hour of methanol vapor, 1,586 kg/hour of steam and 4,020 kg/hour of air.

The reaction gases-formaldehyde, water and residual methanol-were condensed in a customary absorption plant after being cooled in the reactor condenser, and the exit gas was additionally washed with water, which was re-used in the absorption of formaldehyde.

During an operating time of 80 days, an approx. 37.5% strength by weight formaldehyde solution was obtained continuously, having a residual methanol content which varied between 1.0 and 1.8% by weight. The table below shows how the residual methanol content in the formaldehyde altered:

| | Residual methanol content (determined by gas chromatography) in % by weight | Formaldehyde concentration in % by weight |
|---|---|---|
| 1st day | 1.0 | 37.3 |
| 3 days | 1.05 | 37.6 |
| 5 days | 1.25 | 37.3 |
| 7 days | 1.7 | 37.8 |
| 10 days | 1.35 | 37.2 |
| 20 days | 1.4 | 37.5 |
| 40 days | 1.6 | 37.4 |
| 60 days | 1.75 | 37.3 |
| 80 days | 1.8 | 37.5 |

During this operating time, the yield of formaldehyde was about 86 to 89% of theory. As shown by the increasing residual methanol content of the formaldehyde solution produced, the activity of the catalyst fell off as the running time increased.

The catalyst contained a number of extraneous metals and was additionally contaminated by carbon deposits.

What is claimed is:

1. A process for production of formaldehyde which comprises:
   (A) passing fresh methanol or methanol/water mixture through a bed of acid and/or basic ion exchanger and thereafter vaporizing a portion of said methanol or methanol/water mixture feed in a vaporizer whereby some of the methanol or methanol/water mixture remains in liquid phase;
   (B) passing the vapor containing a methanol or methanol/water mixture to a reaction vessel to which oxygen or an oxygen containing gas is introduced and therein converting the methanol to formaldehyde in the presence of a silver catalyst;
   (C) withdrawing at least a portion of said liquid phase and passing said liquid phase over an acid and/or basic ion exchanger; and (D) recycling the liquid phase after contact with said acid and/or basic ion exchanger to said vaporizer.

2. A process according to claim 1 wherein the liquid phase from the vaporizer is passed through an acid and/or basic ion exchanger through which fresh methanol or methanol/water mixture is passed.

3. A process according to claim 1 wherein the liquid phase from the vaporizer is passed through an acid and/or basic ion exchanger different from that through which fresh methanol or methanol/water mixture is passed.

4. A process according to claim 1, wherein said vaporizer is operated at a temperature of 60° C. to 100° C.

5. A process according to claim 1, wherein said vaporizer is operated at a temperature of 65° C. to 75° C.

6. A process according to claim 1, wherein said vaporizer is operated at a pressure of 0.5 atmosphere to 2.0 atmospheres.

7. A process according to claim 1, wherein said vaporizer is operated at a pressure of 0.7 to 1.5 atmospheres.

8. A process according to claim 1, wherein the feed rate for said methanol or methanol/water mixture is 1000 to 4000 liters/hour.

9. A process according to claim 1, wherein the feed rate for said methanol or methanol/water mixture is 1500 to 4000 liters/hour.

10. A process according to claim 1, wherein said liquid phase is passed through said vaporizer at a feed rate of 500 to 1500 liters/hour.

11. A process according to claim 1, wherein said liquid phase is passed through said vaporizer at a feed rate of 800 to 1200 liters/hour.

12. A process according to claim 1, wherein said liquid phase is at a temperature of 65° C. to 75° C.

13. A process according to claim 1, wherein said methanol/water mixture contains 55 to 70 weight percent methanol.

* * * * *